United States Patent [19]
Larkin et al.

[11] Patent Number: 4,840,621
[45] Date of Patent: Jun. 20, 1989

[54] PIERCING PIN TRANSFER DEVICE

[75] Inventors: Mark E. Larkin, Lindenhurst; John E. Ogden, Libertyville, both of Ill.

[73] Assignee: Abbott Laboratories, Abbott Park, Ill.

[21] Appl. No.: 145,008

[22] Filed: Jan. 19, 1988

[51] Int. Cl.⁴ .............................................. A61M 5/00
[52] U.S. Cl. ...................................... 604/29; 604/411; 141/330
[58] Field of Search .......................... 604/29, 411–414, 604/905; 141/298, 330; 222/83, 83.5, 89

[56] References Cited

U.S. PATENT DOCUMENTS

| | | | |
|---|---|---|---|
| 4,500,788 | 2/1985 | Kulin et al. | 604/29 X |
| 4,541,829 | 9/1985 | Munsch et al. | 604/411 X |
| 4,557,727 | 12/1985 | Handt | 604/411 X |
| 4,655,753 | 4/1987 | Bellotti et al. | 604/29 X |

Primary Examiner—Stephen C. Pellegrino
Attorney, Agent, or Firm—Robert E. Wexler; Michael J. Roth

[57] ABSTRACT

A device for automatically transferring a piercing pin from the port of one medical liquid container to the port of another medical liquid container. The ports are mounted to the device in opposing relationship. The piercing pin is inverted at an intermediate position between the ports.

27 Claims, 5 Drawing Sheets

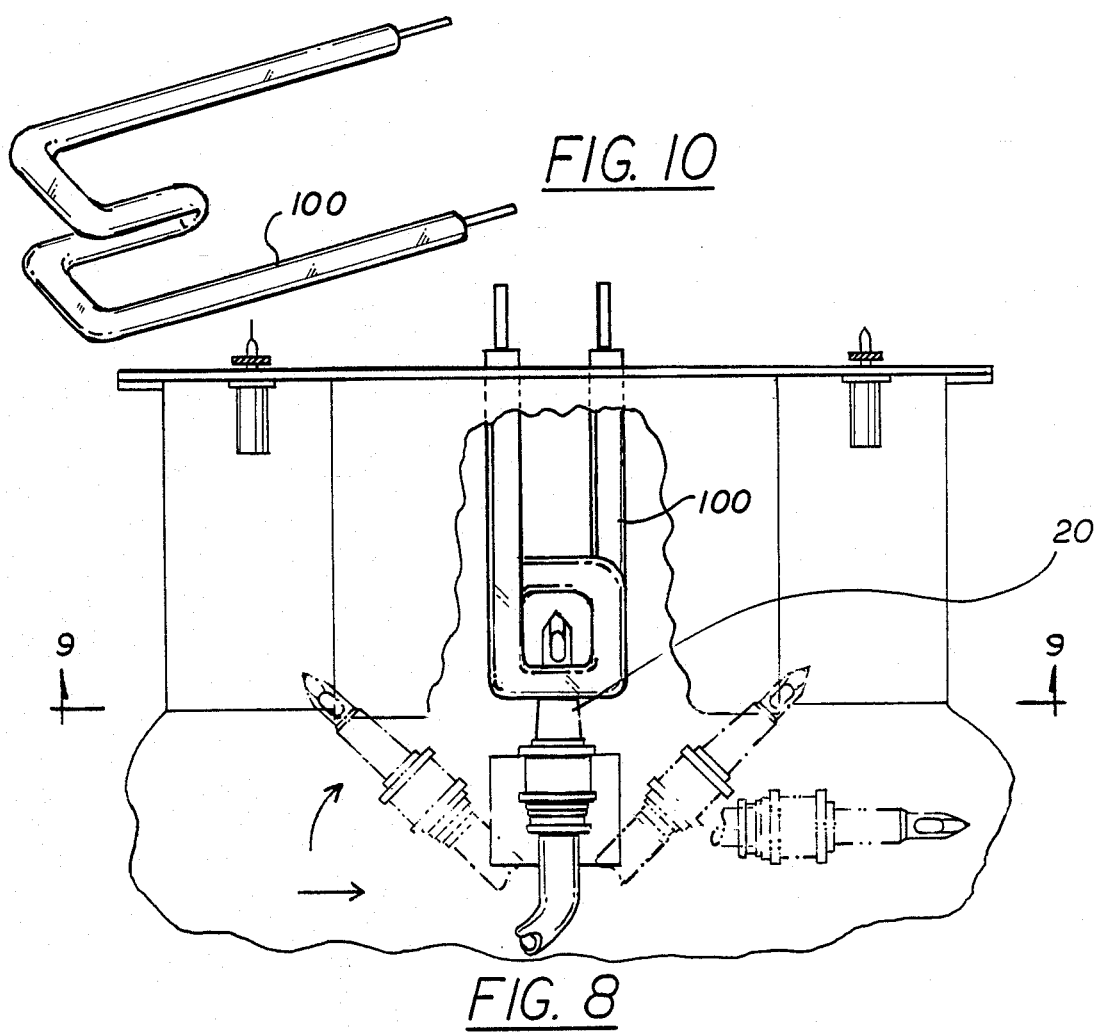
FIG. 10
FIG. 8
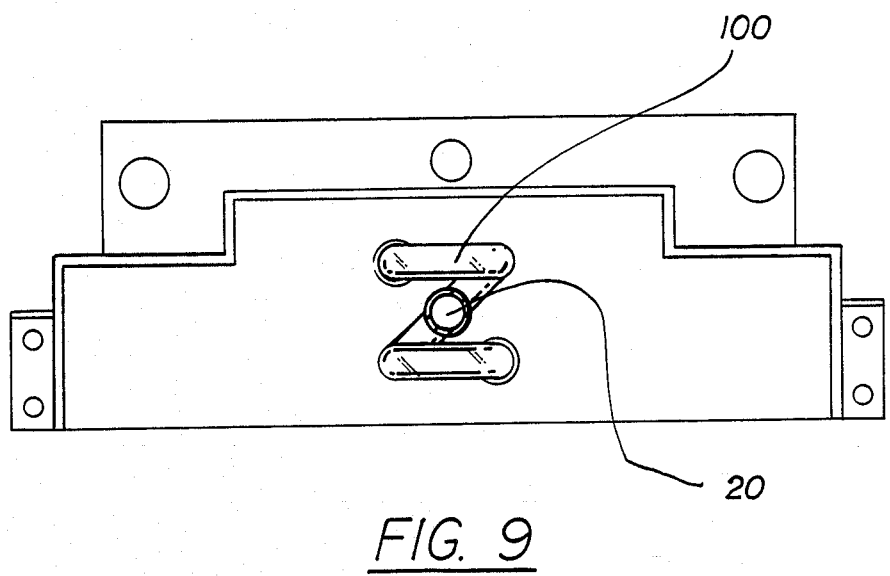
FIG. 9

PIERCING PIN TRANSFER DEVICE

BACKGROUND

This invention relates to the field of medical devices, and more particularly to those devices used to transfer a piercing pin from the port of one tube set to the port of another tube set.

One particularly important application for the present invention is in the field of peritoneal dialysis, where it is used for the treatment of chronic renal failure. In peritoneal dialysis, body waste is removed from the blood by placing a dialysis solution within the peritoneal cavity of the abdomen (through a permanent catheter in the patient) and allowing the solution to remain for a period of time. During this dwell period, waste material from the blood diffuses across the peritoneal membrane (a smooth transparent serous membrane lining the cavity of the abdomen), and into the dialysis solution placed within the peritoneal cavity. The fluid is then drained from the peritoneal cavity, through the permanent catheter and into a bag. A tubular piercing pin, which is attached to the permanent catheter, via a tube set is then transferred from the bag of spent dialysis solution to a bag of new dialysis solution. The new dialysis solution is then drained into the peritoneal cavity to begin the dialysis process again. The empty bag is rolled up during the dwell time, thus providing a high degree of mobility to the patient.

Chronic peritoneal dialysis, however, is not without its limitations. Because the permanent catheter is an open conduit into the patient's peritoneal cavity, there is a potential for introduction of bacteria and development of peritonitis. Patients utilizing this technique must therefore exchange the bag of spent dialysis solution for the bag of new dialysis solution under highly sterile conditions. Traditionally, this has required that the connections between the catheter and the dialysis solution bags be treated with antibacterial agents. The difficulty of maintaining adequately sterile conditions using such methods is compounded by the fact that many patients suffering from renal failure (and thus requiring some form of dialysis) are visually and/or strength impaired, or lack sufficient manual coordination to carry out the procedures necessary to maintain sterile conditions. Such patients also have difficulty transferring the piercing pin from an old to a new bag of dialysis solution.

A number of devices have been developed to assist patients in exchanging dialysis solution bags while maintaining sterile conditions. For example, U.S. Pat. No. 4,655,753 discloses a device having a lever for manually exchanging a piercing pin from a first container to a second container without touch contamination by the user. U.S. Pat. No. 4,541,82 discloses a similar device having a track that guides a piercing pin from a first container to a second container. U.S. Pat. No. 4,500,788 discloses a device for removing a piercing pin from a container by moving a lever upward, and inserting a piercing pin into a new container by moving the lever downward. The piercing pin and connecting portion of the container are subjected to ultraviolet radiation. U.S. Pat. Nos. 4,557,727 and 4,405,315 disclose a device having a manually operated lever whose motion is limited by a track for guiding the piercing pin from one container to another container.

Although such devices exchange the piercing pin without the user having to touch the connections, the exchange still requires manual operation. Patients with extreme strength impairment can have difficulty even with these devices. Since these devices are operated manually, there is also a possibility that the patients using devices equipped with UV sterilizing bulbs may not allow the connections sufficient time to become completely sterile under ultraviolet radiation. Thus, most devices still rely on the physical ability and judgment of the patient to assure sterile conditions.

SUMMARY OF THE INVENTION

The present invention is a device for automatically transferring a piercing pin from the port of one medical liquid container to the port of another medical liquid container. The ports are mounted in opposing relationship, and means is provided for disconnecting the piercing pin from one port, inverting the pin at an intermediate position between the two ports, and connecting it to the other opposing port.

In one aspect of the present invention, the piercing pin is mounted on a rotatable carrier that travels along a linear path to and from the two opposing ports. At a point intermediate the two opposing ports, the rotatable carrier is rotated, thus inverting the piercing pin so that it can be inserted into the opposing port.

In another aspect of the present invention, means is provided for inverting the piercing pin carrier (together with the piercing pin) at an intermediate position between the opposing tube sets. The piercing pin carrier is fixedly connected with a shuttle block, preferably by means of a rod which is connected to the piercing pin carrier, extends through the lead screw follower, and is connected to the shuttle block. The shuttle block is guided along a linear path between the opposing ports by guiding means that are parallel with the lead screw. The shuttle block has two slots for receiving two fixed indexing pins which are positioned in the linear path at intermediate points between the opposing tube sets, but are offset from the linear path of the axis of rotation of the shuttle block. As the shuttle block is moved along the linear path, the slots in the cam receive the indexing pins and rotate the shuttle block.

In yet another aspect of the present invention, a source of ultraviolet radiation is provided for sterilizing the piercing pin while it is being inverted. In a particularly preferred embodiment, the source of ultraviolet radiation is a single bulb located at an intermediate point between the opposing ports. During inversion of the piercing pin, the piercing pin is stopped at an intermediate point and subjected to ultraviolet radiation.

BRIEF DESCRIPTION OF THE DRAWINGS

FIG. 8 is a fragmentary sectional top view of the piercing pin in relation to the UV bulb of the device of FIGS. 1-6;

FIG. 9 is a sectional side view of a UV bulb with the piercing pin in its center, as shown in FIG. 8;

FIG. 10 is a perspective view of a preferred UV bulb of the present invention, as shown in FIGS. 6, 8 and 9.

DETAILED DESCRIPTION OF THE PREFERRED EMBODIMENTS

Figure 1:
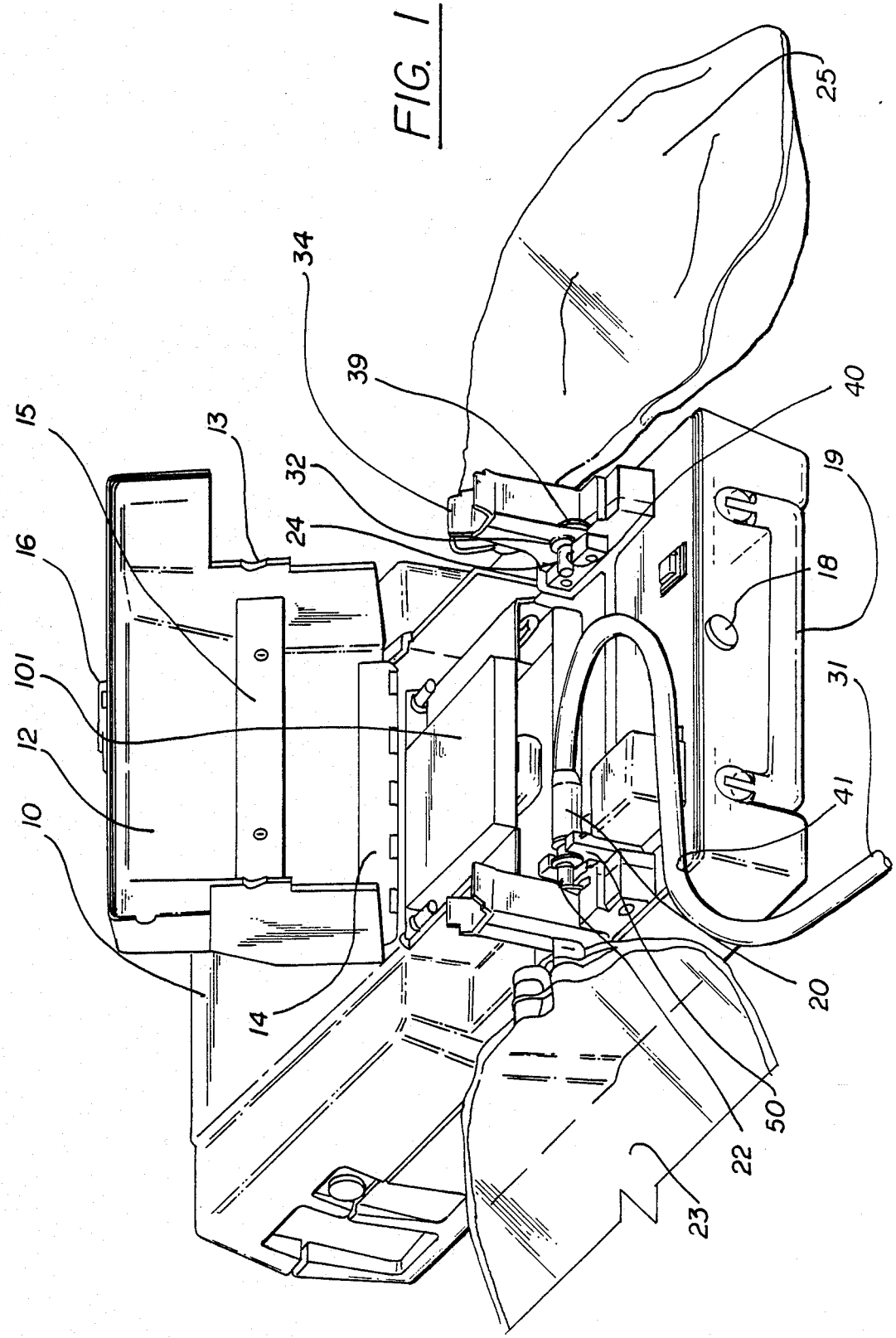
FIG. 1 is a perspective view of the transfer device of the present invention with the lid in the open position.

Referring to FIG. 1 of the drawings, the piercing pin transfer device of the present invention is generally provided with a housing 10 having a lid 12. Lid 12 is connected to the housing by means of a hinge 14 so that lid 12 can be opened and closed. In the open position, access is permitted to the interior cavity. A latch 16 and latch button 18 are provided for releasably securing the lid 12 in its closed position. For convenience, the device shown is equipped with a swing-out handle 19 so that the device can be easily carried.

The housing 10 can be made of various materials and can be formed by various means. It is advantageous, however, to form the housing of materials that are lightweight and resistant to breakage and corrosion, such as plastic or stainless steel. The housing is also preferably sized to be conveniently carried in one hand.

Figure 3:
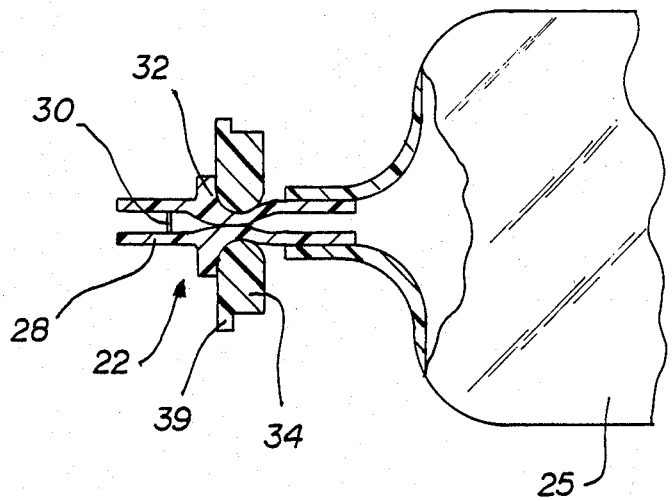
FIG. 3 is a fragmentary sectional view of a container of peritoneal dialysis solution as held by the device of the present invention as shown in FIG. 1.

With reference to FIGS. 1 and 3, the specific application for which the present invention was developed is the transfer of a piercing pin 20 from a first port 22 of a container 23 of spent dialysis solution to a second port 24 of a container 25 of new dialysis solution. Containers of dialysis solution are commercially available, for example, from Abbott Laboratories, North Chicago, Ill. 60064. These containers have a capacity of approximately two liters. As illustrated in FIG. 3, with respect to the second container 25, the container is provided with a flexible tubular port 22 having a sheath 28 for receiving a piercing pin, a pierceable diaphragm 30 positioned within the port, and a radial flange 32 extending outwardly from the port at a point behind the sheath 28.

Figure 2:
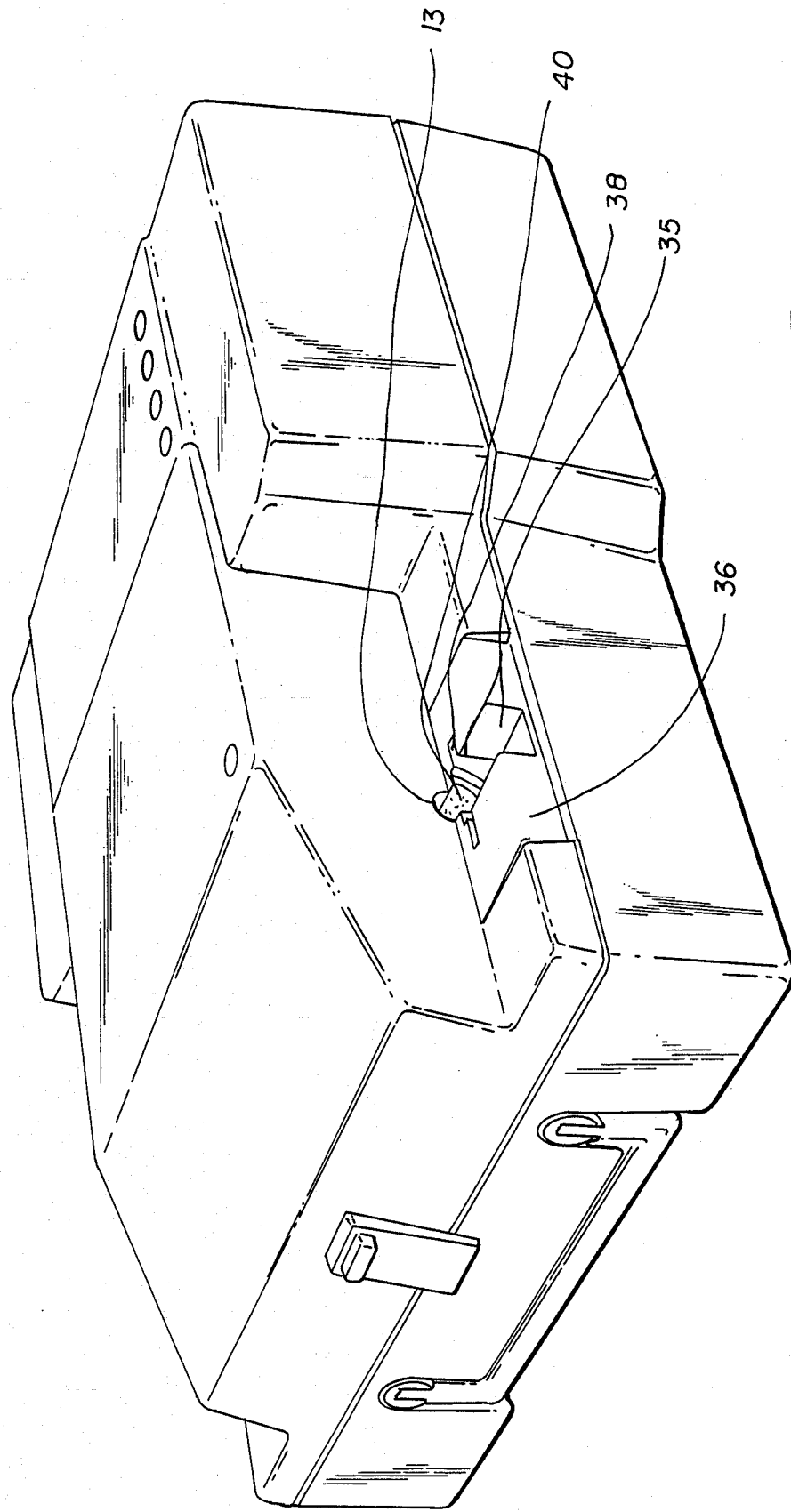
FIG. 2 is a perspective view of the device of FIG. 1 with the lid closed.

With reference to FIGS. 1-3, each bag of peritoneal dialysis solution is held fixed in place by a retaining means. One such retaining means comprises a conventional clamp 34 (shown in FIGS. 1 and 3), for closing port 22 at a point behind the radial flange 32, thereby preventing spillage of dialysate upon puncture of diaphragm 30 in port 22. Clamp 34 is received in slot 35 of support 36. Support 36 is also provided with transverse slot 38 for receiving flange 39 of clamp 34, and a semi-cylindrical slot 40 for receiving port 22. Lid 12 has a radial slot 13 which, when the lid is closed, cooperates with sheath slot 40 to form an aperture through which the sheath 28 extends. This retaining means provides additional stability to port 22 during removal and insertion of piercing pin 20. A second similar retaining means is provided on the opposite side of the housing.

Figure 6:
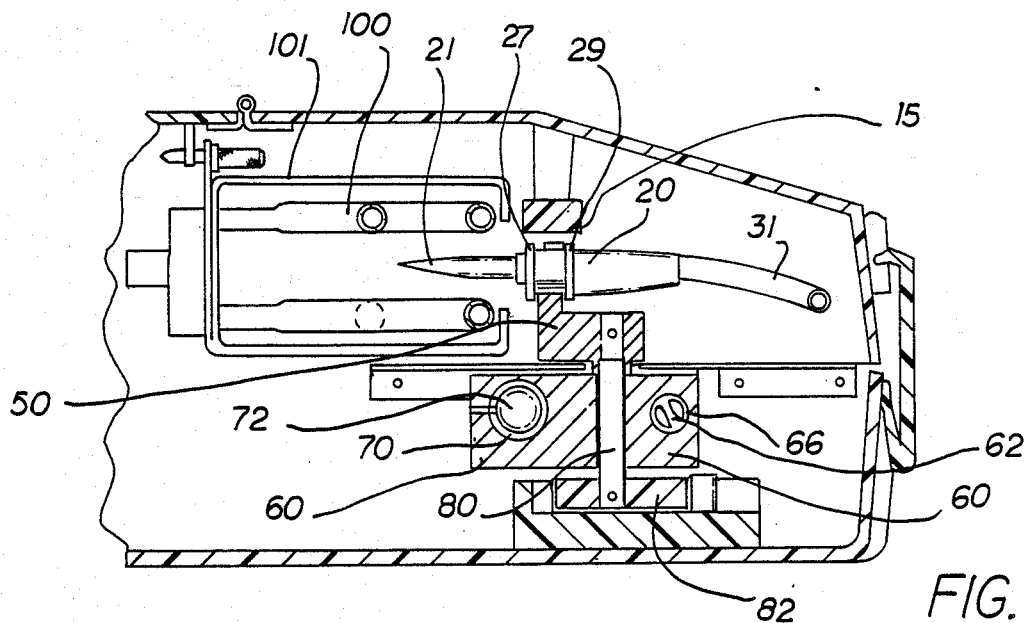
FIG. 6 is a partial sectional side view of the transferring and inverting mechanisms of FIGS. 4 and 5.
Figure 7:
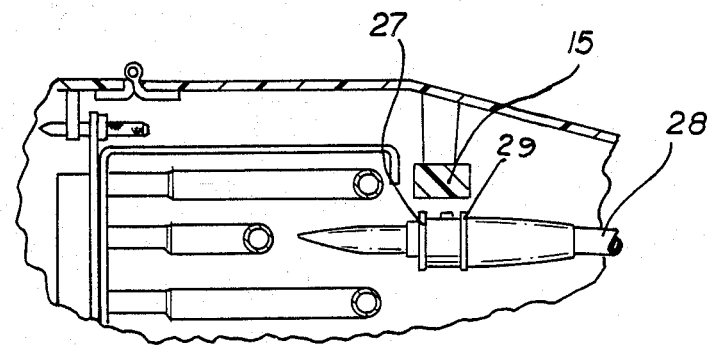
FIG. 7 is a partial sectional side view of an alternative UV source design.

As seen most clearly in FIGS. 6 and 7, the piercing pin 20 has a pointed end 21 for piercing the diaphragm 30 of port 22. Piercing pin 20 is also provided with two outwardly extending radial flanges 27 and 29. The piercing pin is attached to a flexible tubing set 31 which extends out of aperture 41 of the housing (see FIG. 1) to a catheter implanted in the patient's peritoneal cavity.

Figure 4:
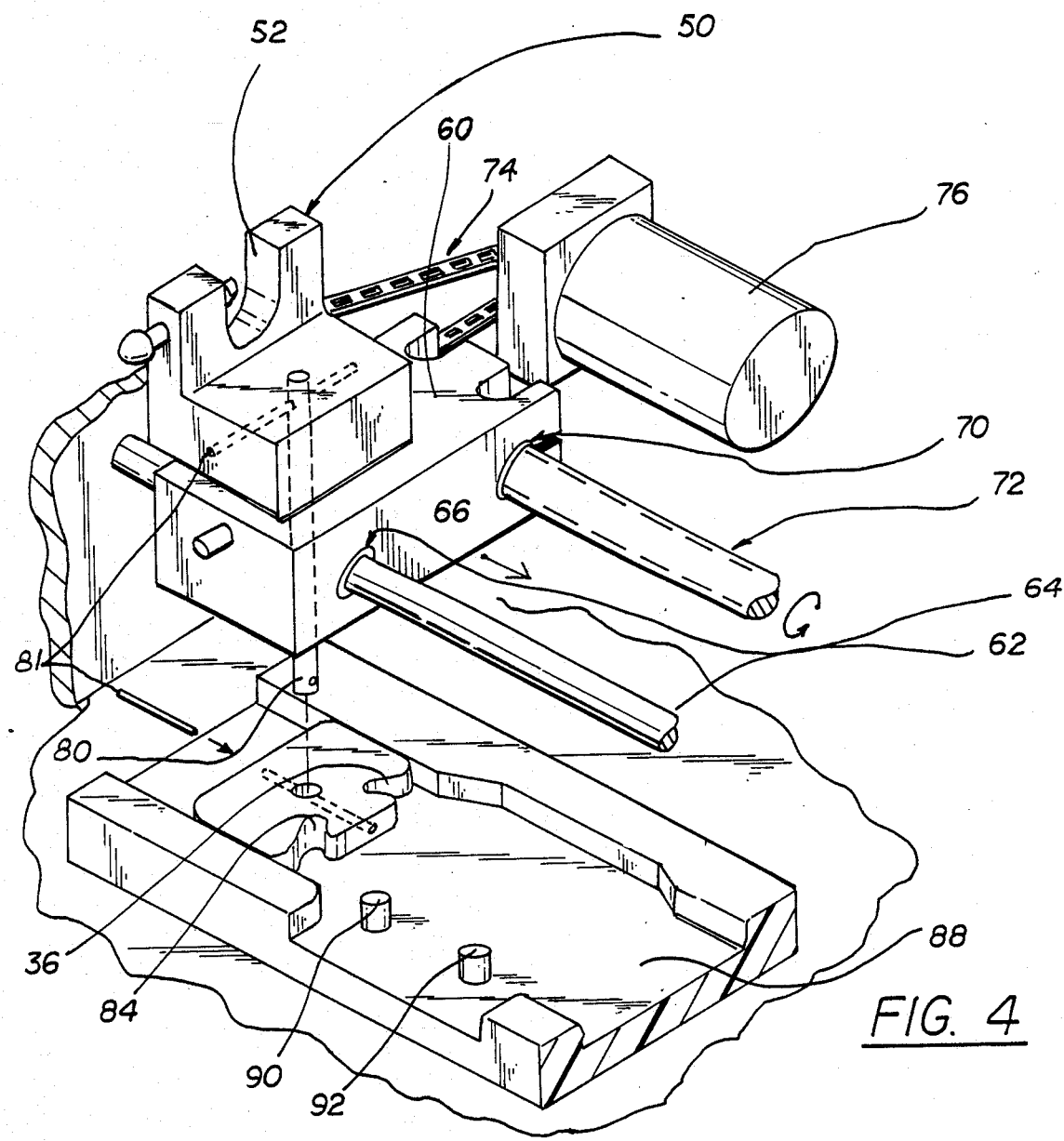
FIG. 4 is an exploded perspective view of the mechanism for transferring and inverting the piercing pin of the device of FIG. 1.

With reference to FIGS. 1, 4, and 6, in particular, a piercing pin carrier 50 is provided to hold the piercing pin 20. Carrier 50 includes a generally U-shaped slot 52 adapted to receive the portion of piercing pin 20 between radial flanges 27 and 29. The radial flanges 27 and 29 prevent the piercing pin 20 from being displaced from the piercing pin support. Means is also provided for retaining the piercing pin 20 in slot 52. For example, a retaining strip 15 is attached to the inside of lid 12 and is positioned so that when lid 12 is in the closed position the retaining strip 15 is positioned on the top of piercing pin carrier 50 for the entire length of the linear travel of the piercing pin carrier 50 to and from opposing ports. Accordingly, radial flanges 27 and 29 prevent lateral movement of piercing pin 20, and the retaining strip 15 prevents vertical movement, thus securing piercing pin 20.

The piercing pin carrier 50 transfers piercing pin 20 from the first port 22 to the opposing second port 24. Piercing pin 20 is first disconnected from the first port 22, inverted approximately 180 degrees while moving from the first port 22 to the second port 24, and then connected to the second port 24. In the presently preferred embodiment, piercing pin carrier 50 travels along a linear path from the two opposing ports 22 and 24. At an intermediate position between the first port 22 and second port 24, the carrier 50 is rotated approximately 180 degrees about a vertical axis. The piercing pin 20 is most advantageously positioned on carrier 50 such that when the carrier 50 is rotated the point 21 of piercing pin 20 is offset from the linear path of carrier 50. As will be explained in more detail below, this enables the piercing pin 20 to be subject to ultraviolet irradiation from an ultraviolet bulb which is positioned to the side of the linear path of the carrier 50.

As seen in FIGS. 4 and 6, the carrier 50 is rotatably mounted on a lead screw follower 60. Lead screw follower 60 is guided along a linear path between first port 22 and second port 24 by a linear guide means, such as a stabilizer rod 62 that is parallel with the linear path. The stabilizer rod 62 extends through a bushing 66 which is set in a cylindrical hole 64 through the lead screw follower 60. The bushing 66 serves as a guide for the stabilizer rod 62 and minimizes abrasion of the stabilizer rod 62 and lead screw follower 60.

Lead screw follower 60 is also provided with a power nut 70 which is fixedly secured in a cylindrical hole through the shuttle block. An acme threaded lead screw 72, which is parallel with the linear guide means, is threadably engagable with an acme threaded power nut 70. When lead screw 72 is rotated about its longitudinal axis, the power nut 70 (and lead screw follower to which it is secured) moves along the lead screw 72 in a linear path. The lead screw 72 is connected by drive belt 74 to a drive means 76, such as a motor.

Means is also provided for inverting the piercing pin support (together with the piercing pin) at an intermediate position between opposing ports. As mentioned above, the piercing pin carrier 50 rotatably rests on lead screw follower 60. Carrier 50 is fixedly connected with a rotation rod 80 which extends vertically through the lead screw follower 60 and is fixedly connected to a shuttle block 82. The rotation rod 80 is connected to the carrier 50 by means of a pin 81 inserted into the side of the carrier, through the rotation rod 80, and back into the carrier. A similar connection is made between the rotation rod 80 and the shuttle block 82. Rotation of the shuttle block 82 thus causes rotation of the piercing pin carrier 50.

The shuttle block 82 is guided along a linear path by guiding means 88. In the presently preferred embodiment, the shuttle block 82 is substantially rectangular, with first slot 84 and second slot 86 in the two inside corners. The shuttle block 82 is disposed in a guide means 88 having a width at each end substantially equal to the width of said shuttle block 82 such that the shuttle block cannot rotate. At the location where the shuttle block is to be rotated, a first fixed indexing pin 90 and second fixed indexing pin 92 are mounted along the path of one edge of the shuttle block 82 offset from the linear path of the axis of rotation of the rotation rod 80. At this point, the width of the guide means 88 is also widened to accommodate rotation of the shuttle block. The first and second indexing pins 90 and 92 respectively and sequentially engage first and second radial slots 84 and 86 of the shuttle block 82 in response to linear movement of the shuttle block 82 in along guide means 88.

Figure 5:
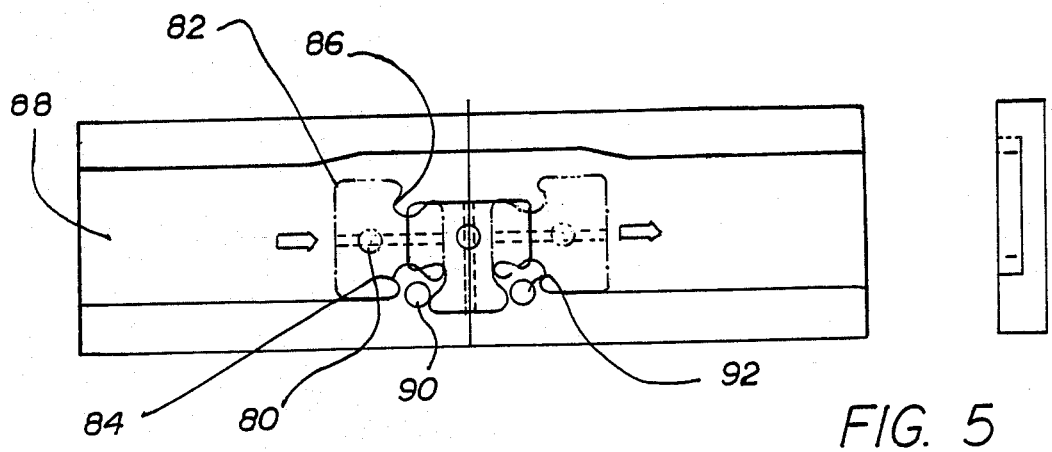
FIG. 5 is a partial sectional top view of the shuttle block and indexing pin assembly used to invert the piercing pin, as shown in FIG. 4.

As shown in FIG. 5, as shuttle block 82 moves linearly along the guide means 88, first radial slot 84 engages first indexing pin 90, causing shuttle block 82 to pivot 90 degrees thereabout. Rotation of shuttle block 82 brings second radial slot 86 into engagement with second indexing pin 92, causing shuttle block 82 to pivot an additional 90 degrees about indexing pin 92. Thus, a 180 degree rotation is effected in response to linear movement of the shuttle block 82.

With reference to FIGS. 8, rotation of the piercing pin 20 through 180 degrees causes the tip 21 of the piercing pin to swing to the side out of the linear path of travel of the axis of rotation. In one preferred embodiment of the present invention, a source of ultraviolet radiation 100, such as an ultraviolet bulb, is provided to sterilize the piercing pin while it is being inverted. The UV source 100 is positioned so that the piercing pin 20 is radiated from the front and all sides. This can be done, as shown in FIG. 7, for example, by shaping several UV bulbs to follow the path above, below and in front of the tip 21.

In the presently preferred embodiments of this device, the ultraviolet source 100 is a single UV bulb having a design as shown in FIG. 10. The UV bulb 100 is positioned within a chamber 101 to protect the bulb and prevent patient exposure to UV radiation. In order to assure proper sterilization of piercing pin 20, it is desirable to stop inversion of piercing pin 20 to allow sufficient time for irradiation.

The electronics and electrical supply system carried in the apparatus of this invention may be of any desired design for providing the desired energy to UV bulb 100. The particular electronics used herein do not constitute the invention of this application.

Essentially, the electronics may include, if desired, an electronic microprocessor and memory which supervises operation of the device and enables failure mode alarms so that the user can determine the operability of the system, and a cycle-complete indicator, when desired to indicate to the user that the sterilization cycle is complete.

Conventional safety interlocks may be used so that the UV bulb 100 is shut off if lid 12 is opened. Likewise, a system may be provided which is responsive to the total UV energy supplied, so that the UV bulb is shut off when a prescribed amount of energy has been emitted. A light sensor may also be provided to communicate through a logic circuit with the lamp power supply, controlling the power supply to lamp 100, so that the UV light emitted provides a desired luminous flux.

The apparatus is powered by conventional rechargeable batteries, such as gel cell battery. The on/off switch is inaccessible any time that the lid is closed. Once this switch is thrown, only failure of one of the safety checks will abort the transfer process. The unit checks for (1) adequate battery power to complete the entire transfer process; (2) proper placement of bags, clamps and connectors; (3) closure of the lid throughout the transfer; and (4) proper operation of the UV bulb. The unit identifies completion of the transfer by measuring motor current which is correlated with motor load. When the motor current reaches a value which indicates the piercing pin is completely seated in the bag port, the operation is terminated.

Movement of the spike from one position to another can be regulated by means of a series of switches located in the path of the lead screw follower as it moves between the opposing ports. Each switch indicates the position of the piercing pin 20.

The position information can be interpreted by an electronic microprocessor and compared with a series of instructions stored in an electronic memory. The microprocessor authorizes continued operation of the device, unless a combination of conditions is encountered which is interpreted as outside the limits stored in memory. When such limits are exceeded the microprocessor enables an appropriate alarm device (such as a lamp and/or electroacoustic device) to alert the user to an unsatisfactory condition.

Printed circuit wiring may be provided for interconnection of the desired logic and memory electronics of the system. Suitable specific circuitry is readily constructed by those skilled in the art.

Although the present invention has been described in connection with presently preferred embodiments, those skilled in the art will recognize many modifications to sequence, arrangement, portions, elements, and materials which can be used in the practice of the invention without departing from its scope. It is intended that such changes and modifications be covered by the following claims.

We claim:

1. A piercing pin transfer device comprising, in combination
   a piercing pin;
   means to support said pin;
   means for holding a first port adapted to connect to said pin;
   means for holding a second port adapted to connect to said pin, said second port holding means being in opposing relationship with said first port holding means;
   means for connecting said pin to said first port, disconnecting said pin from said port, and connecting said pin to said second port and
   means for inverting said piercing pin intermediate of said first port holding means and said second port holding means.

2. The device of claim 1 further comprising means for sterilizing said piercing pin while said piercing pin is being inverted.

3. The device of claim 2, wherein said sterilizing means is a source of ultraviolet irradiation.

4. The device of claim 3, wherein said ultraviolet irradiation source is at a position intermediate of said first and second port holding means.

5. The device of claim 4 further comprising means for moving said piercing pin between said first and second port holding means and means for stopping movement of said piercing pin at said intermediate position.

6. The device of claim 5, wherein said ultraviolet irradiation source radiates from above, below, and in front of said piercing pin at said intermediate position.

7. The device of claim 6, wherein said ultraviolet irradiation source is a single bulb.

8. A piercing pin transfer device comprising in combination
a piercing pin, removably mounted in a support therefor;
means for carrying said piercing pin;
means for holding a first port adapted to connect to said piercing pin;
means for holding a second port adapted to connect to said piercing pin, said second port holding means being in opposing relationship with said first port holding means;
means for housing said piercing pin carrying means and for transferring said piercing pin from said first port holding means to said opposing second port holding means along a linear path defined by linear guide means;
means for inverting said piercing pin carrying means while transferring said piercing pin carrying means along said linear path; and
wherein said transfer from said first port holding means disconnects said piercing pin from said first port, said piercing pin carrier means inverts said piercing pin, and said transfer to said second port connects said piercing pin to said opposing second port.

9. The device of claim 8 further comprising means for sterilizing said piercing pin while said piercing pin is being inverted.

10. The device of claim 9, wherein said sterilizing means is a source of ultraviolet irradiation.

11. The device of claim 10, wherein said ultraviolet irradiation source is at a position intermediate of said first and second port holding means.

12. The device of claim 11 further comprising means for stopping movement of said piercing pin at said intermediate position.

13. The device of claim 12, wherein said ultraviolet irradiation source radiates from above, below, and in front of said piercing pin at said intermediate position.

14. The device of claim 13, wherein said ultraviolet irradiation source is a single bulb.

15. The device of claim 8, wherein said linear guide means comprises:
a lead screw follower supporting said piercing pin carrying means, said lead screw follower having an integral power nut;
a lead screw threadably engaged with said power nut;
a linear guide means guiding said lead screw follower along a linear path; and
means for reversibly driving said lead screw to thereby move said lead screw follower between said first and second port holding means.

16. The device of claim 15 further comprising means for sterilizing said piercing pin while inverting said piercing pin.

17. The device of claim 16, wherein said sterilizing means is an ultraviolet light source.

18. The device of claim 17, wherein said piercing pin is sterilized with ultraviolet irradiation at an intermediate position between the first and second port holding means.

19. The device of claim 18 further comprising means for stopping movement of said piercing pin at said intermediate position.

20. The device of claim 19, wherein said ultraviolet irradiation at said intermediate position is above, below, and in front of said piercing pin.

21. The device of claim 8, wherein said means for inverting said piercing pin carrying means comprises:
a shuttle block having two radial slots; means for fixedly and rotatably connecting said shuttle block with said piercing pin carrying means;
means for guiding said shuttle block along a linear path; and
two fixed indexing pins disposed in said linear path at a point offset from the linear path of the axis of rotation of said shuttle block, said indexing pins being disposed to engage said radial slots and rotate said shuttle block as said shuttle block is moved along said linear path, thereby rotating said piercing pin carrying means.

22. The device of claim 21 further comprising means for sterilizing said piercing pin while inverting said piercing pin.

23. The device of claim 22, wherein said sterilizing means is an ultraviolet light source.

24. The device of claim 23, wherein said piercing pin is sterilized with ultraviolet irradiation at an intermediate position.

25. The device of claim 24 further comprising means for stopping movement of said piercing pin at said intermediate position.

26. The device of claim 25, wherein said ultraviolet irradiation at said intermediate position is above, below, and in front of said piercing pin.

27. A piercing pin transfer device comprising, in combination:
a housing;
means for carrying a piercing pin, mounted in said housing;
a piercing pin removably mounted in said carrying means;
a first port for receiving said piercing pin;
a second port for receiving said piercing pin, said second port being in opposing relationship with said first port;
means for moving said piercing pin carrying means along a linear path from said first port to said second port;
means, disposed in said housing, for holding said first and second ports;
means, disposed in said housing, for rotating said piercing pin carrying means 180 degrees while moving said piercing pin carrying means along said linear path, thereby inverting said piercing pin;
wherein said linear movement of said piercing pin causes withdrawal of said piercing pin from said first port, and insertion of said piercing pin into said second port; and
means for providing ultraviolet irradiation of said piercing pin between said first and second port.

* * * * *